(12) United States Patent
Ma

(10) Patent No.: US 6,623,732 B1
(45) Date of Patent: Sep. 23, 2003

(54) PHARMACEUTICAL FORMULATION FOR NASAL ADMINISTRATION

(75) Inventor: Xin Fang Ma, Beijing (CN)

(73) Assignees: Highchem Company, Ltd., Tokyo (JP); Charna Chemicals Ltd., Beijing (CN)

( * ) Notice: Subject to any disclaimer, the term of this patent is extended or adjusted under 35 U.S.C. 154(b) by 0 days.

(21) Appl. No.: 09/674,519

(22) PCT Filed: Apr. 1, 1999

(86) PCT No.: PCT/JP99/01704

§ 371 (c)(1), (2), (4) Date: Jan. 8, 2001

(87) PCT Pub. No.: WO99/59543

PCT Pub. Date: Nov. 25, 1999

(30) Foreign Application Priority Data

May 20, 1998 (CN) ........................... 98108852 A

(51) Int. Cl.$^7$ ........................ A61K 9/00; A61K 47/20; A61K 47/48

(52) U.S. Cl. ........................ 424/85.4; 424/434; 514/2; 514/3; 514/12; 514/15; 514/16; 514/21; 514/772; 514/777

(58) Field of Search ............... 424/85.4, 434; 514/2, 3, 8, 12, 21, 15, 16, 772, 777

(56) References Cited

U.S. PATENT DOCUMENTS

| 5,137,875 | A | * | 8/1992 | Tsunenaga et al. | ........... 514/21 |
| 5,416,071 | A | | 5/1995 | Igari et al. | ............ 514/8 |
| 5,578,567 | A | * | 11/1996 | Cardinaux et al. | ............ 514/12 |
| 5,591,713 | A | | 1/1997 | Igari et al. | ............ 514/8 |
| 6,039,970 | A | | 3/2000 | Callegaro et al. | ........... 424/434 |
| 6,066,340 | A | | 5/2000 | Callegaro et al. | ........... 424/499 |

FOREIGN PATENT DOCUMENTS

| CN | 88106763 | 9/1988 |
| CN | 95119260 | 11/1995 |
| EP | 0364235 | 4/1990 |
| EP | 418642 A1 | 3/1991 |
| EP | 0588255 | 3/1994 |
| JP | 1-294633 | 11/1989 |
| JP | 2-000213 | 1/1990 |
| JP | 3-99021 | 4/1991 |
| JP | 3-246233 | 11/1991 |
| JP | 5-97694 | 4/1993 |
| JP | 5-186362 | 7/1993 |
| JP | 6-199681 | 7/1994 |
| JP | 7-118170 | 5/1995 |
| JP | 7-179363 | 7/1995 |
| JP | 8-198772 | 8/1996 |
| JP | 9-309843 | 12/1997 |
| WO | 89/02279 | 3/1989 |
| WO | 98/43664 | 10/1998 |

OTHER PUBLICATIONS

English Language Abstract of JP 3–246233. (Nov. 1991).
English Language Abstract of JP 5–97694. (Apr. 1993).
English Language Abstract of JP 9–309843. (Dec. 1997).
Partial English translation of JP 2–000213 (Jan. 1990).
English Language Abstract of JP 8–198772. (Aug. 1996).
English Language Abstract of JP 1–294633. (Nov. 1989).
English Language Abstract of JP 7–118170. (May 1995).
English Language Abstract of JP 3–99021. (Apr. 1991).
Merkus et al., "The influence of absorption enhancers on intranasal insulin absorption in normal and diabetic subjects", Journal of Controlled Release, vol. 41, pp 69–75 (1996).
Partial English translation of Chinese application 95–119260.4 (Nov. 1995).

* cited by examiner

Primary Examiner—Jeffrey E. Russel
(74) Attorney, Agent, or Firm—Greenblum & Bernstein, P.L.C.

(57) ABSTRACT

This invention discloses a pharmaceutical formulation for nasal administration which contains a pharmaceutically active polypeptide and a method producing the pharmaceutical formulation. The pharmaceutical for formulation comprises: (1) a pharmaceutically active polypeptide, (2) at least one compound selected from the group consisting of taurine, an ester thereof with C1~6 alcohol, a base metal salt of taurine, hyaluronic acid and a base metal of hyaluronic acid and (3) at least one pharmacologically acceptable additive. It exhibited excellent pharmaceutical activity. No adverse effects such as irration were observed and hence, the present pharmaceutical formulation may suitably be administered nasal mucosa.

33 Claims, No Drawings

PHARMACEUTICAL FORMULATION FOR NASAL ADMINISTRATION

TECHNICAL FIELD

The present invention relates to a pharmaceutical formulation of nasal administration containing a pharmaceutically active polypeptide, and particularly relates to a pharmaceutical formulation for nasal administration that comprises at least one compound selected from the group consisting of taurine, an ester thereof with C18 6 alcohol, a base metal salt of taurine, hyaluronic acid and a base metal salt of hyaluronic acid. These compounds are used as absorbefacients for the pharmaceutical formulation of the present invention. The pharmaceutical formulation of the present invention may be dosed through nasal mucosa. The present invention also relates to a method for producing the pharmaceutical formulation.

BACKGROUND ART

A powder composition for nasal administration including a physiologically active peptide with a hyaluronic acid butyrene glycol ester as a carrier is disclosed in Japanese Patent Publication (laid-open) No. 6-199681. A pharmaceutical composition for administration through nasal mucosa, with preferably a pH of about 4, containing a peptide hormone and hyaluronic acid or its salt is disclosed in Japanese Patent Publication (laid-open) No. 3-246233. A microsphere formed comprising a physiologically active peptide that is surrounded by hyaluronic acid esters or which is adsorbed on hyaluronic acid esters is disclosed in Japanese Patent Publication (laid-open) No. 7-179363. A pharmaceutical formulation with improved drug delivery comprising a physiologically active peptide, hyaluronic acid or a non-toxic salt of these compounds, and polymer substance is disclosed in Japanese Patent Publication (laid-open) No. 5-97694. A pharmaceutical formulation for administration through the lung that comprises peptide type drugs and hyaluronic acid is disclosed in Japanese Patent Publication (laid-open) No. 9-309843. A pharmaceutical formulation with sustained physiological activity comprising hyaluronic acid or its non-toxic salts is disclosed in Japanese Patent Publication (laid-open) No. 2-213. A powder pharmaceutical formulation for nasal administration that contains a granulocyte colony stimulating factor, saccharides, hyaluronic acid or its salt is disclosed in Japanese Patent Publication (laid-open) No. 8-198772. An eye drop containing insulin and hyaluronic acid or its salt as a thickening agent is disclosed in Japanese Patent Publication (laid-open) No.1-294633. An aqueous pharmaceutical composition with sustained pharmaceutical activity that contains a pharmaceutically active peptide, water soluble hyaluronic acid, and a water soluble protein which does not exhibit pharmaceutical activity is disclosed in Japanese Patent Publication (laid-open) No. 5-186362. A peptide composition having a physiologically active peptide homogenously dispersed in a carrier hyaluronic acid so that it is adhesively bound to the carrier is disclosed in Japanese Patent Publication (laid-open) No. 7-118170. A super-absorbent drug for administration through vagina that contains the absorbefacient taurine in a bioactive polypeptide is disclosed in Japanese Patent Publication (laid-open) No. 3-99021. In Chinese Patent Application No. 95119260.4, an absorbefacient for absorption of peptide containing pharmaceuticals through mucosae is disclosed. The absorbefaciens disclosed in the above Chinese application include azone, saponins, glycyrrhizionic acid, and esters, salts of these compounds, glycyrrhetinic acid and a sodium salt of glycyrrhetinic acid, dihydroxymorintannic acid and its derivatives, and carboxylic acid estes of these compounds. However, the only formulation example disclosed in the above Chinese Patent Application is a sublingual tablet containing such absorbefaciens. In Chinese Patent Application No. 88106763.6, a pharmaceutical formulation for administration through mucosae is disclosed. The absorbefaciens contained in the formulation are monosaccharides such as D-erythrose, D-ribose, D-ribulose, D-xylose, D-arabinose, D-mannose, L-sorbose, D-sedumtheptulose, or monosacarides such as α-cyclodextrin, β-cyclodextrin, γ-cyclodextrin, and cyclodextrin having side chains.

Polypeptide compounds are easily degraded with enzymes in the human stomach and intestines and are easily metabolized in the human liver. Therefore, polypeptide compounds are difficult to give their intrinsic pharmaceutical effects in a patient's body. Thus, polypeptide compounds are generally administration as various injections such as hypodermic injections, intramuscular injections, and intravenous injections. However, the patient experiences pain and irritation such as, for example, injury and necrosis of his/her muscle tissue during long-term polypeptide administration of the injections and there is potential for infections caused by injection due to communicable diseases. The patient also experiences various inconveniences such as the need to receive regular outpatient treatment. For these reasons, extensive studies have recently been made to administer the polypeptide compounds through mucosae such as the nasal mucosa, no polypeptide containing pharmaceutical formulations for administration through the nasal mucosa have not yet been commercially available.

Therefore, polypeptide containing pharmaceutical formulations for administration through nasal mucosa are highly desired and their development has been waited for a long term.

An object of the present invention is to provided a pharmaceutical formulation for nasal administration containing a pharmaceutically active polypeptide and also to provide a method for producing thereof.

SUMMARY OF THE INVENTION

The inventor has found a novel pharmaceutical formulation suitable for nasal administration and succeeded in accomplishing the present invention as the result of the study to solve the above problems. The novel pharmaceutical formulation containing a pharmaceutically active polypeptide exhibits high pharmaceutical activity as high as the pharmaceutical activity obtained in the administration through injection and does not irritate patients.

According to the present invention, the pharmaceutical formulation for nasal administration comprises (1) a pharmaceutically active polypeptide, (2) at least one compound selected from the group consisting of taurine, an ester thereof with C1~6 alcohol, an base metal salt of taurine, hyaluronic acid and a base metal salt of hyaluronic acid, and (3) at least one pharmacologically acceptable additive.

Further according to the present invention, the pharmaceutical formulation for nasal administration preferably comprises (1) a pharmaceutically active polypeptide, (2) at least one compound selected from the group consisting of taurine, an ester thereof with C1~6 alcohol, a base metal salt of taurine, (3) at least one compound selected from hyaluronic acid and a base metal salt of hyaluronic acid, and (4) at least one pharmacologically acceptable additive.

Further according to the present invention, the pharmaceutical formulation for nasal administration more preferably comprises (1) a pharmaceutically active polypeptide, (2) taurine and hyaluronic acid, and (3) at least one pharmacologically acceptable additive.

Further according to the present invention, the pharmaceutical formulation may comprise at least one compound selected from the group consisting of taurine, an ester thereof with C1~6 alcohol, a base metal salt of taurine, hyaluronic acid, a base metal salt of hyaluronic acid and a mixture thereof or a carrier for the pharmaceutically active polypeptide for administration through the nasal mucosa.

In accordance with the present invention, a method for producing a pharmacological formulation is also provided. The method for producing a pharmaceutical formulation for nasal administration containing of at least one pharmaceutically active polypeptide comprises the steps of;

adding an adequate amount of distilled water to a compound selected from the group consisting of taurine, an ester thereof with C1~6 alcohol, a base metal salt of taurine, hyaluronic acid, a base metal salt of the hyaluronic acid, a mixture thereof, and an optional additive to form a solution of the ingredients;

adjusting the pH of the solution formed by dissolving the compounds; and adding a pharmaceutically active polypeptide to the solution and dissolving the pharmaceutically active polypeptide.

Further according to the present invention, the method for producing the pharmaceutical formulation may further include the steps of:

filtering the solution for sterilization thereof; and filling a bottle with the filtrate.

BEST MODE FOR CARRYING OUT THE INVENTION

In the present invention, examples of the pharmaceutically active polypeptide include natural insulin obtained from cow and pig or synthetic insulin, calcitonin, hirudin, glucagon, angiotensin, lactation hormone, growth hormone, thyroid-stimulating hormone (THS) or thyrotropin, adrenocorticotropin, and interferon, and mixtures thereof.

In a preferred embodiment of the present invention, a pharmaceutical formulation to be administered through the nasal mucosa for treatment of diabetes is provided. The pharmaceutical formulation of the preferred embodiment contains insulin as the above pharmaceutically active polypeptide.

The base metal salt of taurine is used as one of the absorbefacients which is contained in the pharmaceutical formulation for nasal administration according to the present invention. Exemplary base metal salts may include sodium salts of taurine and potassium salts of taurine, and the like. The base metal salt of hyaluronic acid is used as one of the absorbefacients which is contained in the pharmaceutical formulation for nasal administration according to the present invention. Exemplary of base metal salts may include sodium salts of hyaluronic acid and potassium salts of hyaluronic acid, and the like.

Insulin is one of the effective ingredients of the pharmaceutical formulation for nasal administration of the present invention and examples may include natural insulin obtained from cow and pig, synthetic insulin and insulin produced by a recombinant DNA technique.

Diabetes which is to be treated with the insulin-containing pharmaceutical formulation for nasal administration of the present invention may be type I diabetes or type II diabetes.

The pharmaceutical formulation for nasal administration of the present invention may be preferably formulated as a liquid drop type drug or a spray type drug. The pharmaceutical formulation for nasal administration of the present invention which may be provided either as a liquid drop type drug or as a spray type drug may be dosed, for example, through the nasal mucosa to a human.

The pharmaceutically active polypeptide containing pharmaceutical formulation of the present invention may possibly formulated from the pharmaceutically active polypeptide together with an absorbefacient and/or a carrier. However, the inventor has found that significant therapeutic effect is obtained when the pharmaceutical formulation for nasal administration includes simultaneously the pharmaceutically active polypeptide, absorbefacient taurine or a derivative thereof and carrier hyaluronic acid or a derivative thereof.

The pharmaceutically active polypeptide containing pharmaceutical formulation for nasal administration of the present invention may preferably contain 0.01~20 w/v % of at least one absorbefacient compound selected from taurine, its ester with C1~6 alcohol, and its base metal salt and at least one carrier compound selected from 0.01~10 w/v % of at least one compound selected from hyaluronic acid and its base metal salts, or a mixture thereof.

In the present invention, an aqueous solution containing a pharmaceutically active polypeptide or a pharmaceutical formulation for nasal administration, the pH may generally range from 6 to 8, more preferably range from 6.5 to 7.5.

The pharmaceutical formulation for nasal administration of the present invention which contains a pharmaceutically active polypeptide may be produced, for example, according to the following steps;

adding an adequate amount of distilled water to a compound selected from the group consisting of taurine, its ester with C1~6 alcohol, its base metal salt, hyaluronic acid, its base metal salt of the hyaluronic acid, a mixture thereof, and an optional additive such as, for example, a preserving agent Nipagin A (p-hydroxybenzoic acid ethyl ester) to form a solution of the ingredients;

adjusting the pH of the solution to between 6.5 and 7.5, more preferably to about 7.0, with 0.1 N HCl or 0.1N NaOH after dissolving the compounds by heating the mixture; and adding a pharmaceutically active polypeptide such as insulin to the above solution and dissolving the pharmaceutically active polypeptide.

The above process may optionally includes the steps of:

filtering the above solution for sterilization thereof; and filling a bottle with the filtrate. The bottle may be specially produced for this purpose.

According to the present invention, the dose of the pharmaceutically active polypeptide containing pharmaceutical formulation for administration through the nasal mucosa may vary with patient's age, body weight, health condition, the severity of the disease, drugs to be simultaneously administered, their kinds, and the kinds of the pharmaceutically active polypeptides. Generally, the dose of the pharmaceutical formulation for nasal administration of the present invention which contains a pharmaceutically active polypeptide may be determined according to known doses of the pharmaceutically active polypeptide used.

EXAMPLES

Embodiments of the present invention are further explained by the following particular examples. These examples are described only for explanation rather than for limiting the scope of the present invention.

Example 1

Production of pharmaceutical formulation for nasal administration:
Formulation:

| Ingredients | Amount |
| --- | --- |
| Insulin | 20000 IU |
| Taurine | 2 g |
| 0.1N HCl or 0.1N NaOH | adequate amount |
| Nipagin A (p-hydroxy benzoic acid ethyl ester) | 0.03 g |
| Distilled water | make to 100 ml |

To the mixture of taurine and Nipagin A, an adequate amount of distilled water was added, then the mixture was heated to dissolve the ingredients. After dissolving the ingredients, the solution was adjusted to pH=7 with 0.1N HCl or 0.1N NaOH. After that, insulin was added to the solution. After insulin was dissolved, the solution was filtered for sterilization thereof. The resulting filtrate was charged into a specially made sterilized bottle.

Example 2

Production of pharmaceutical formulation of nasal administration:
Formulation:

| Ingredients | Amount |
| --- | --- |
| Insulin | 20000 IU |
| Hyaluronic acid | 0.5 g |
| 0.1N HCl or 0.1N NaOH | adequate amount |
| Nipagin A (p-hydroxy benzoic acid ethyl ester) | 0.03 g |
| Distilled water | make to 100 ml |

To the mixture of hyaluronic acid and Nipagin A, an adequate amount of distilled water was added, then the mixture was heated to dissolve the ingredients. After dissolving the ingredients, the solution was adjusted to pH=7 with 0.1N HCl or 0.1N NaOH. After that, insulin was added to the solution. After insulin was dissolved, the solution was filtered for sterilization thereof. The resulting filtrate was charged into a specially made sterilized bottle.

Example 3

Production of pharmaceutical formulation for nasal administration:
Formulation:

| Ingredients | Amount |
| --- | --- |
| Insulin | 20000 IU |
| Taurine | 2 g |
| Hyaluronic acid | 1 g |
| 0.1N HCl or 0.1N NaOH | adequate amount |
| Nipagin A (p-hydroxy benzoic acid ethyl ester) | 0.03 g |
| Distilled water | make to 100 ml |

To the mixture of taurine, hyaluronic acid and Nipagin A, an adequate amount of distilled water was added, then the mixture was heated to dissolve the ingredients. After dissolving the ingredients, the solution was adjusted to pH=7 with 0.1N HCl or 0.1N NaOH. After that, insulin was added to the solution. After insulin was dissolved, the solution was filtered for sterilization thereof. The resulting filtrate was charged into a specially made sterilized bottle.

Example 4

The insulin-containing pharmaceutical formulation for nasal administration was formulated as a collunarium or a nasal drop type drug according to the present invention. The pharmaceutical formulation was examined with respect to the blood sugar level in alloxan diabetes of rats caused by administration by alloxan injections. Control experiments were simultaneously conducted under the same conditions.

Materials

Animal: Animals used were Wistar rats, male, body weight between 200 g and 220 g, which were purchased from Chinese Military Medical Animal Center with certificate number: Beijin Testing Animal Control Number (1994) No. 052:

The pharmaceutical formulation containing insulin according to the present invention: three different dose levels of 10 IU/kg, 5 IU/kg, 2.5 IU/kg were used in the examples.

Reagent and Instruments

Alloxan: Commercially available alloxan made in Hong Kong, Lot No. FL0610021153: UV-VIS spectrophotometer: Commercially available UV-VIS spectrophotometer made in Japan:

Experimental Procedure

Healthy rats were selected from the above Wistar rats and fasted for 24 hr, except that they were allowed to drink water ad libitum. After fasting, a solution of 40 mg/kg of an alloxan salt was intravenously injected to each rat. After 36 hr from the injection of alloxan, the rats were fasted for 12 hr, except that they were allowed to drink water ad libitum. After additional 12 hr, an experiment was started. In the experiment, the sugar level of collected blood was measured. The blood was collected after injecting an anesthetic to the rats. The anesthetic and its dose were sodium pentobarbital and 30 mg/kg per rat, respectively. An experiment was also conducted using a blank control group, a model group, and a treated group. The blank control group was a group in which the rats were not administered alloxan by injection while the rats in the other two groups were injected alloxan. The rats in the blank control group and the model group were administered a control pharmaceutical formulation which had the same composition as the formulation of the present invention except that they contained no insulin. The administration to these two groups was made by dropping the control pharmaceutical formulation to their nostrils. The control pharmaceutical formulation was dropped in 10

μl/100 g. For rats in the treated group, the pharmaceutical formulations for nasal administration according to the present invention containing 10 IU insulin/kg, 5 IU insulin/kg, or 2.5 IU insulin/kg were dosed by dropping into their nostrils with the same amount of the pharmaceutical formulation (10 μl/100 g) as for the blank control group and the model group. Blood was collected from the rats in each group after 1 hr, 2 hr, 3 hr, and 4 hr from the administration of the formulation according to the present invention. The result is shown in Table 1.

According to the data in Table 1, the insulin-containing pharmaceutical formulation according to the present invention is easily absorbed by the nasal mucosa and exhibits significant blood sugar level lowering effects.

INDUSTRIAL APPLICABILITY

The pharmaceutical formulation for nasal administration which contains a pharmaceutically active polypeptide according to the present invention exhibited excellent pharmaceutical activity. No adverse effects such as irritation on the nasal mucosa were observed. Therefore, it is concluded that the pharmaceutical formulation according to the present invention is an excellent pharmaceutical formulation for administration through nasal mucosa.

TABLE 1

Pharmaceutical effects of insulin-containing nasal drop drugs on the alloxan induced high blood sugar levels of the Wistar rats when they were administered through nasal mucosa

| Time after Administration | Group | Dose | Number of rats per group | Percentage of rats with lowered blood sugar level (%) | Decrease in blood sugar level (mg/dl) | Decrease in blood sugar level (%) |
|---|---|---|---|---|---|---|
| 1 hr | Blank group | 10 μl/100 g | 10 | 60 | 5.9 ± 3.1 | 8.5 ± 5.1 |
| | Model group | 10 μl/100 g | 10 | 60 | 27.1 ± 16.9 | 11.3 ± 8.7 |
| | Treated group | 10 IU/kg | 10 | 100 | 53.3 ± 17.5 | 18.8 ± 7.3 |
| | Treated group | 5 IU/kg | 10 | 100 | 46.0 ± 20.7 | 17.1 ± 7.8 |
| | Treated group | 2.5 IU/kg | 10 | 100 | 36.7 ± 17.0 | 13.2 ± 6.3 |
| 2 hrs | Blank group | 10 μl/100 g | 10 | 60 | 8.1 ± 4.6 | 11.0 ± 6.3 |
| | Model group | 10 μl/100 g | 10 | 30 | 6.5 ± 5.5 | 1.9 ± 1.6 |
| | Treated group | 10 IU/kg | 10 | 100 | 89.2 ± 44.2 | 29.6 ± 10.9 |
| | Treated group | 5 IU/kg | 10 | 100 | 59.3 ± 32.0 | 21.4 ± 10.0 |
| | Treated group | 2.5 IU/kg | 10 | 100 | 48.6 ± 37.6 | 16.8 ± 11.2 |
| 3 hrs | Blank group | 10 μl/100 g | 10 | 30 | 5.1 ± 2.1 | 7.2 ± 3.0 |
| | Model group | 10 μl/100 g | 10 | 20 | 9.8 ± 9.7 | 2.6 ± 1.8 |
| | Treated group | 10 IU/kg | 10 | 100 | 75.6 ± 51.8 | 24.3 ± 13.9 |
| | Treated group | 5 IU/kg | 10 | 90 | 46.1 ± 22.6 | 16.6 ± 6.8 |
| | Treated group | 2.5 IU/kg | 10 | 80 | 43.8 ± 35.9 | 14.9 ± 11.6 |
| 4 hrs | Blank group | 10 μl/100 g | 10 | 0 | 0 | 0 |
| | Medel group | 10 μl/100 g | 10 | 0 | 0 | 0 |
| | Treated group | 10 IU/kg | 10 | 100 | 56.3 ± 53.6 | 16.8 ± 15.9 |
| | Treated group | 5 IU/kg | 10 | 80 | 19.3 ± 10.8 | 6.8 ± 3.5 |
| | Treated group | 2.5 IU/kg | 10 | 80 | 31.2 ± 29.8 | 10.4 ± 9.3 |

IU: International Unit

While the present invention has been explained by referring to specific examples, it is possible for a person skilled in the art to make variations and modifications of the embodiments described above without departing from the scope of the invention. The scope of the present invention is limited only by the appended claims and not by the examples described above.

I claim:

1. A pharmaceutical formulation for nasal administration, which comprises (1) a pharmaceutically active polypeptide (2) taurine and hyaluronic acid, and (3) at least one pharmacologically acceptable additive.

2. The pharmaceutical formulation for nasal administration according to claim 1, wherein the pharmaceutically active polypeptide is selected from the group consisting of insulin, calcitonin, hirudin, glucagon, angiotensin, a lactation hormone, a growth hormone, a thyroid-stimulating hormone or thyrotropin, adrenocorticotropin, and interferon.

3. The pharmaceutical formulation for nasal administration according to claim 2, wherein the pharmaceutically active polypeptide is insulin.

4. The pharmaceutical formulation for nasal administration according to claim 1, wherein the pharmaceutical formulation is a drop type formulation or a spray type formulation.

5. A pharmaceutical formulation for nasal administration, which comprises (1) a pharmaceutically active polypeptide, (2) 0.01~20 w/v % of at least one compound selected from the group consisting of taurine, an ester thereof with C1~6 alcohol, and a base metal salt of taurine, (3) at least one compound selected from the group consisting of hyaluronic acid and a base metal salt of hyaluronic acid, and (4) at least one pharmacologically acceptable additive.

6. A pharmaceutical formulation for nasal administration, which comprises (1) insulin, (2) 0.01~10 w/v % of at least one compound selected from the group consisting of hyaluronic acid and base metal salt of hayaluronic acid, (3) at least one compound selected from the group consisting of taurine, an ester thereof with C1~6 alcohol, and a base metal salt of taurine and (4) at least one pharmacologically acceptable additive.

7. The pharmaceutical formulation for nasal administration according to claim 5, wherein the at least one compound selected from the group consisting of hyaluronic acid and a base metal salt of hyaluronic acid is present in a concentration of 0.01~10 w/v %.

8. The pharmaceutical formulation for nasal administration according to claim 7, wherein the base metal salt is a sodium or potassium salt.

9. The pharmaceutical formulation for nasal administration according to claim 1, wherein the pharmacologically acceptable additive is at least one compound selected from the group consisting of a preserving agent and an excipient.

10. The pharmaceutical formulation for nasal administration according to claim 9, wherein the pharmacologically acceptable additive contains an excipient and a preserving agent.

11. The pharmaceutical formulation for nasal administration according to claim 9, wherein the excipients water.

12. The pharmaceutical formulation for nasal administration according to claim 9, wherein the preserving agent is p-hydroxybenzoic acid ethyl ester.

13. The pharmaceutical formulation for nasal administration according to claim 9, wherein the pH of the formulation ranges from 6 to 8.

14. The pharmaceutical formulation for nasal administration according to claim 13, wherein the pH of the formulation ranges from 6.5 to 7.5.

15. A pharmaceutical formulation for nasal administration, which is used for therapeutics for diabetes comprising (1) insulin, (2) taurine and hyaluronic acid, and (3) at least one pharmacologically acceptable additive.

16. The pharmaceutical formulation for nasal administration according to claim 15, wherein the pharmaceutical formulation is a drop type formulation or a spray type formulation.

17. The pharmaceutical formulation for nasal administration according to claim 15, wherein the insulin is obtained from cow or pig or synthetic insulin.

18. The pharmaceutical formulation for nasal administration according to claim 15, wherein the diabetes is of type I diabetes or type II diabetes.

19. A pharmaceutical formulation for nasal administration, which contains (1) insulin, (2) 0.01~20 w/v % of at least one compound selected from the group consisting of taurine, an ester thereof with C1~6 alcohol, and a base metal salt of taurine, (3) at least one compound selected from the group consisting of hyaluronic acid and a base metal salt of hyaluronic acid, and (4) at least one pharmacologically acceptable additive comprising water.

20. A pharmaceutical formulation for nasal administration, which contains (1) insulin, (2) 0.01~10 w/v % of at least one compound selected from the group consisting of hyaluronic acid and a base metal salt of hyaluronic acid, (3) at least one compound selected from the group consisting of taurine, an ester thereof with C1~6 alcohol, and a base metal salt of taurine, and (4) at least one pharmacologically acceptable additive comprising water.

21. The pharmaceutical formulation for nasal administration according to claim 19, wherein the least one compound selected from the group consisting of hyaluronic acid and a base metal salt of hyaluronic acid is present in a concentration of 0.01~10 w/v %.

22. The pharmaceutical formulation for nasal administration according to claim 21, wherein the base metal salt is a sodium or potassium salt.

23. The pharmaceutical formulation for nasal administration according to claim 15, wherein the pharmacologically acceptable additive is at least one compound selected from the group consisting of a preserving agent and an excipient.

24. The pharmaceutical formulation for nasal administration according to claim 23, wherein the pharmacologically acceptable additive contains an excipient and a preserving agent.

25. The pharmaceutical formulation for nasal administration according to claim 23, wherein the excipient is water.

26. The pharmaceutical formulation for nasal administration according to claim 23, wherein the preserving agent is p-hydroxybenzoic acid ethyl ester.

27. The pharmaceutical formulation for nasal administration according to claim 15, which is dosed through nasal mucosa.

28. The pharmaceutical formulation for nasal administration to claim 27, which has a pH in the range from 6 to 8.

29. The pharmaceutical formulation for nasal administration to claim 27, which has a pH in the range from 6.5 to 7.5.

30. A method for producing a pharmaceutical formulation for nasal administration which contains at least insulin, the method comprising:

adding an adequate amount of distilled water to at least one compound selected from the group consisting of taurine, an ester thereof with C1~6 alcohol, and a base metal salt of taurine, and at least one compound selected from the group consisting of hyaluronic acid and a base metal salt of hyaluronic acid to form a solution of the ingredients;

adjusting the pH of the solution formed by dissolving the compounds; and adding insulin to the solution and dissolving the insulin.

31. The method for producing the pharmaceutical formulation according to claim 30, wherein the pH of the solution is between 6.5 and 7.5.

32. The method for producing the pharmaceutical formulation according to claim 30 further including an additive in the solution.

33. The method for producing the pharmaceutical formulation according to claim 30 wherein the at least one compound selected from the group consisting of taurine, an ester thereof with C1~6 alcohol, and a base metal salt of taurine comprises taurine, and the at least one compound selected from the group consisting of hyaluronic acid and a base metal salt of hyaluronic acid comprises hyaluronic acid.

* * * * *

UNITED STATES PATENT AND TRADEMARK OFFICE
CERTIFICATE OF CORRECTION

PATENT NO.     : 6,623,732 B1                                      Page 1 of 1
DATED          : September 23, 2003
INVENTOR(S)    : X. F. Ma It is certified that error appears in the above-identified patent and that said Letters Patent is hereby corrected as shown below:

<u>Title page,</u>
Item [56], References Cited, FOREIGN PATENT DOCUMENTS,
"88106763" should be -- 88106763.6 --; and "95119260" should be -- 95119260.4 --;
Item [30], Foreign Application Priority Data, "98108852A" should be
-- 98108852X --; also the following Priority Application was omitted and should be included:
-- Japan          10/313934          10/19/1988 --
Item [57], ABSTRACT,
Line 4, delete "for".
Line 8, after "metal" insert -- salt --.
Line 11, "irration" should be -- irritation --.
Line 13, before "nasal" insert -- through --.

<u>Column 8,</u>
Line 58, after "taurine" insert -- , --.

<u>Column 9,</u>
Line 10, "excipients" should be -- excipient is --.
Line 21, after "diabetes" insert -- , --.

<u>Column 10,</u>
Line 22, before "to" (first occurrence) insert -- according --.
Line 24, before "to" (first occurrence) insert -- according --.

Signed and Sealed this

Eleventh Day of May, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,623,732 B1  Page 1 of 1
DATED : September 23, 2003
INVENTOR(S) : X. F. Ma It is certified that error appears in the above-identified patent and that said Letters Patent is hereby corrected as shown below:

Title page,
Item [30], Foreign Application Priority Data,
change "Japan    10/313934      10/19/1988" to the following:
  -- Japan           10/313934       10/19/1998 --.

Signed and Sealed this

Seventh Day of September, 2004

JON W. DUDAS
*Director of the United States Patent and Trademark Office*